United States Patent [19]
Taborsky

[11] Patent Number: 5,935,611
[45] Date of Patent: Aug. 10, 1999

[54] ZEOLITIC INHIBITION OF BIOCATALYSIS

[76] Inventor: Jiri Taborsky, 9808 28th Ave. East, Palmetto, Fla. 34221

[21] Appl. No.: 08/967,006

[22] Filed: Nov. 10, 1997

[51] Int. Cl.⁶ .............................. A61K 33/06; A61K 7/16; A61K 31/695
[52] U.S. Cl. .......................... 424/682; 424/49; 424/684; 514/63
[58] Field of Search .................................. 424/682, 684, 424/49; 514/63

[56] References Cited

U.S. PATENT DOCUMENTS

| | | | |
|---|---|---|---|
| 4,775,585 | 10/1988 | Hagiwara et al. | 428/323 |
| 4,824,661 | 4/1989 | Wagner | 424/52 |
| 4,911,898 | 3/1990 | Hagiwara et al. | 423/118 |
| 4,959,268 | 9/1990 | Hagiwara et al. | 428/403 |
| 5,140,949 | 8/1992 | Chu et al. | 119/174 |

*Primary Examiner*—Kevin E. Weddington
*Attorney, Agent, or Firm*—Charles A. McClure

[57] ABSTRACT

Zeolytic inhibition of biocatalysis that is mediated by enzymes conducive to dysfunctional condition of a host or to contamination of a beverage or foodstuff thereof, by administering a natural or synthetic zeolite thereto. A zeolite or equivalent ion-exchanger is administered to the site of a dysfunctional condition catalyzed by an enzyme dependent upon certain ions, whereupon the ions are adsorbed thereby, thus interrupting the dysfunctional condition or abating the contamination. A therapeutic concentration of the zeolite is administered in finely divided condition, whether dry or as an aerosol or as a liquid suspension, and is effective against a variety of bacterial, fungal, protozoan, and viral infections.

7 Claims, 1 Drawing Sheet

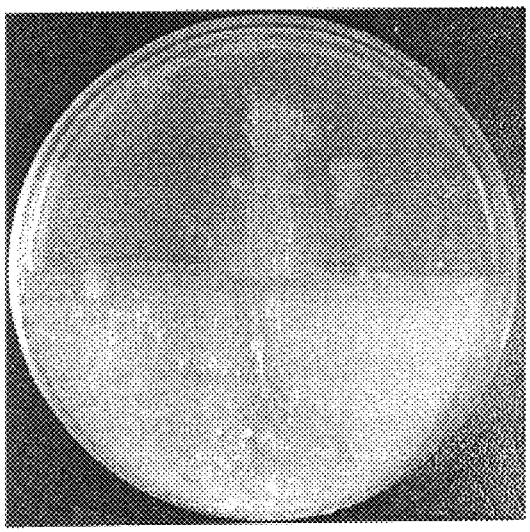
FIG. IA
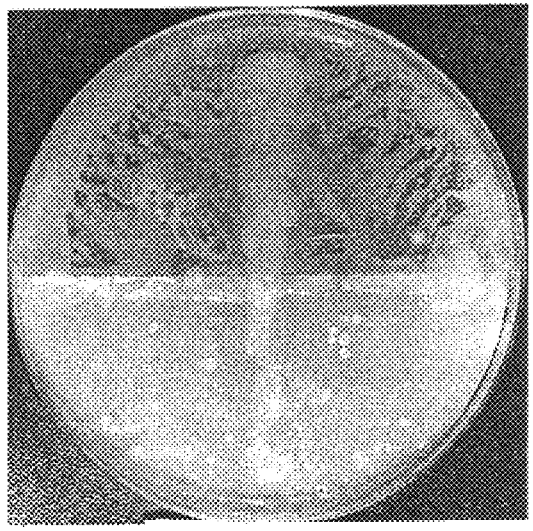
FIG. IB
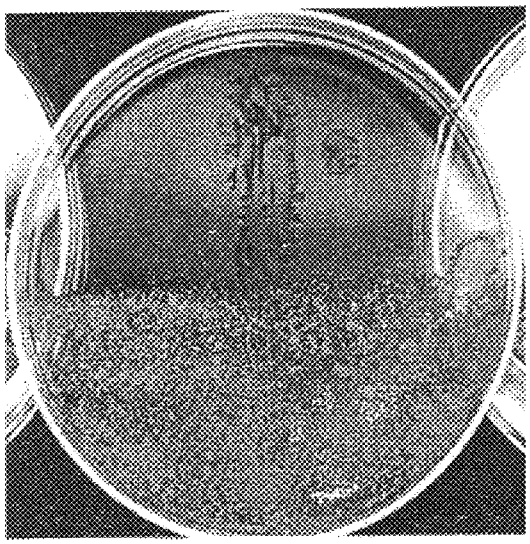
FIG. IC
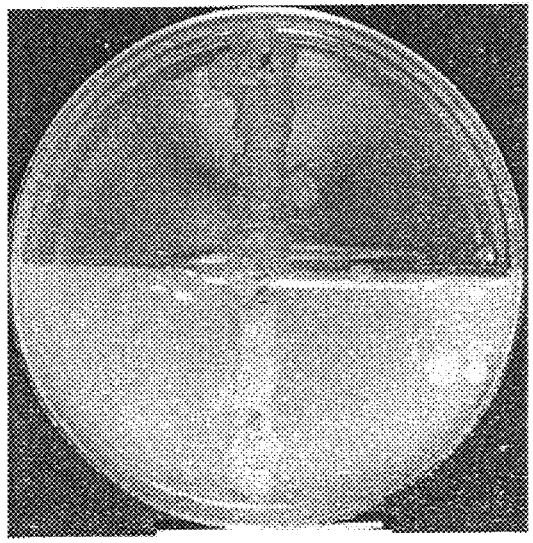
FIG. ID

ZEOLITIC INHIBITION OF BIOCATALYSIS

TECHNICAL FIELD

This invention relates to inhibition of catalysis, especially in biosystems, via interrelations of enzymes, ions, and zeolites.

BACKGROUND OF THE INVENTION

As stated by Bohinski, in *Modern Concepts in Biochemistry*, "the totality of cellular activity is intimately dependent on the type and concentration of ionic materials within the cell—both of which are subject to change by alterations in the extracellular environment." [Allyn & Bacon, Boston, 1973] As stated by Dressler and Potter in *Discovering Enzymes*, "Not to put too fine a point on it, enzymes control all of the chemical transformations in the living world." [SCIENTIFIC AMERICAN LIBRARY, New York, 1991].

Much cellular activity is catalyzed or mediated by enzymes, themselves dependent upon associated ions, as via ion activators or ion-dependent cofactors. In general, the more complex an organism, the more complex and numerous its enzymes become, and the more likely it can survive some enzymatic irregularity, such as inadequate concentration or even absence of a given enzyme. Whereas metabolism in vertebrates depends upon thousands of enzymes, whose activity may require presence of other enzymes or the like, more primitive life forms (e.g., bacteria), get along with fewer enzymes, often controlled only by an ion activator. Primitive biochemical units, such as viruses, which are associated with fewer enzymes, or maybe with only one or part thereof, may have their metabolism or replication ended by enzyme dysfunction.

Where certain biocatalysis is undesirable, interference with associated ions may be beneficial. Whereas Bohinski emphasizes pH as a determining factor, recent researchers have given more weight to susceptibility of enzymes to temperature change, as in "heat shock" treatment, yet others prefer radiation. However, all of these approaches have severe limitations and serious side effects. Researchers in the last decade have focused more upon enzyme inhibitors, usually organic, administered to the host organism, again often causing deleterious side effects.

The present invention directs attention to adsorption of ions or other enzymatic sub-units necessary for biocatalysis via ion-exchangers, such as hydrous aluminosilicate compositions, here exemplified specifically by zeolites, which may be natural or synthetic. Both natural and synthetic zeolites are well known as carriers of ionic substances often intended to catalyze certain chemical activity.

Furthermore, sometimes zeolites are used, either alone or distributed within an organic polymer, to convey an organic toxin, a chelate, or a heavy metal ion as a bactericide or fungicide, as in cosmetics and medicines. See, for example, Yoshimoto et al. U.S. Pat. No. 4,870,107 (1989); Hagiwara et al. U.S. Pat. Nos. 4,775,585 (1988), 4,911,898 (1990), and 4,959,268 (1990).

Many specific uses of zeolites in the role of carriers of substances harmful to biological, sometimes enzyme-dependent, activity are known and could be cited. The present invention utilizes zeolites in a quite different inhibitory manner from such prior art.

SUMMARY OF THE INVENTION

A primary object of the present invention is to inhibit dysfunctional or otherwise undesirable biological activity.

Another object of this invention is to improve sanitation by controlling animal and plant dysfunctions for human benefit.

A further object is to reduce the exposure of the environment to toxic organic and/or metallic substances customarily used in an effort to rid the environment of noxious animal or plant residues.

Yet another object of the invention is to extend such enzyme inhibition to novel areas of agriculture, cosmetics, dentistry, foodstuffs, and medicine.

A still further object is to accomplish the foregoing objects economically and in an environmentally conservative manner.

In general, the objects of this invention are achieved by inhibiting undesirable ion-dependent biological activity, by supplying to the site of that activity a sorbant or ion-exchanger, such as a zeolite, effective to take up ions or related substances essential to such biological activity.

More particularly, the objects are attained by inhibiting the action of enzymes essential to success of the biological activity with which interference is justified, to benefit not only a human host, for example, but also the environment of the host, including animal, human, and plant inhabitants thereof and their foodstuffs.

Natural zeolites may be pretreated for enhancement of their preferences for one ion or related substance over another. Alteration in relative affinities of natural zeolites for given monovalent and divalent ions, by dry heating pretreatment, and benefits of doing so are disclosed in Taborsky U.S. Pat. Nos. 5,082,813; 5,162,276; and 5,304,365. Zeolites or equivalent ion-exchanging compositions may be deionized and be applied as broad-range sorbants, or may be selectively re-ionized for specific applications. Zeolites or equivalent ion-exchanging compositions may even be synthesized with affinities for adsorbing particular ions or classes of ions or for meeting other related purposes.

Other objects of the present invention, together with means and methods for attaining the various objects, will become readily apparent from the following description and accompanying diagrams of various embodiments thereof, presented by way of example rather than limitation.

SUMMARY OF THE DRAWINGS

FIGS. 1A, 1B, 1C, and 1D are photographs of the patterns of growth of given inoculants, each in a separate petri dish, half of which was treated with a zeolite, and half of which was untreated.

DESCRIPTION OF THE INVENTION

The invention is characterized in practical terms, so as to enable its successful practice, regardless of any academic or theoretical misconception expressed in this exposition thereof.

Preliminary Test. A simple test of possible inhibition of enzyme activity by zeolitic adsorption was conducted, using as an indicator ninhydrin (1,2,3-triketohydrindene hydrate), which gives a purple color in the presence of amino acids. At room temperature, 100 mg of bacterial protease was stirred into 100 ml distilled water containing 10 g of deionized phillipsite particles (300>600 $\mu$m). After about 10 minutes of mild agitation, the solution was filtered through a 200 $\mu$m nylon sieve, then 10 ml of the filtrate was stirred thoroughly into 50 ml standard casein solution, which tested negatively to ninhydrin an hour thereafter. A like solution of casein and protease lacking such additive tested positively on the same ninhydrin reagent by turning purple, indicating presence of free amino acids from enzymatic breakdown of the casein. The tentative conclusion was that the zeolite had adsorbed cations from the enzyme (protease) and inhibited it from breaking the casein down and providing amino groups for detection. Similar inhibition of enzymatic activity by zeolites can be shown in various settings, such as agriculture, dentistry, and medicine.

Agriculture. A plant's immune system is quite rudimentary in comparison with the complex immune systems of highly organized animals, such as mammals, so antibiotics and especially xenobiotics, such as most bactericides and viricides, have severe limitations. Where even limited applicability exists, the cost usually is so excessive as to be prohibitive. As a rule, the simpler an organism, the less its immune capability. For example, simple organisms have only a few cytochrome P450 enzymes available and capable of deactivating a xenobiotic, whereas higher organisms have a complex array of defenses. Too, many plants and most phytopathogens are not sufficiently differentiated in their organizational complexity to provide reasonable assurance that what will kill the pathogen won't also kill the plant. This is a noteworthy feature taken into account by the present invention.

FIG. 1A illustrates laboratory results mirroring the experimental outcomes of investigation of agricultural infestation in citrus trees by bacteria harmful to both foliage and fruit, and abatement thereof by application of zeolitic material thereto. This experimentation was stimulated by news of a recent outbreak of citrus canker, which is caused by *Xanthomonas citri* (syn. *X. campestris*) believed to occur in three pathotypes. Florida recognizes only one treatment: uprooting and burning of all the infested trees, a drastic, dubious and extremely expensive remedy.

Regulations possibly affecting cultivation of such pathogens suggested that in vitro testing be conducted using some related but non-regulated species; *Pseudomonas fluorescens* was selected.

A standard Plate Count Agar was selected as the medium in a petri dish. The surface was smear-inoculated with such bacteria, then the lower half of the plate was dusted with small (<300 $\mu$m) particles of a selected zeolite: phillipsite. As shown in FIG. 1A, normal bacterial growth resulted in a distinct plume (upper half), where the zeolite was absent, whereas bacterial growth was entirely inhibited by the zeolite on the treated lower half.

This experimentation was extended to in vivo treatment of four-to-six years old pink grapefruit and navel orange trees, the two most canker-susceptible varieties of citrus (Rutaceae). Signs of infection appeared on about 5% of the leaves and occasional fruit, with incipient defoliation and premature abscission of some fruit. One particular tree, noticeably smaller than the others, showed about half of all its leaves infected, some branches already bare, and significant loss of fruit. The grove as a whole showed untreated leaf miner damage, which is generally believed to facilitate entry of phytopathogens, such as citrus canker here.

Phillipsite particles (600–710 $\mu$m) were partially deionized by washing with distilled water (11 g/liter), then were dried at room temperature and finally were reduced to smaller particles (≦75 $\mu$m).

The resulting wettable powder was applied as a spray (10 g/liter) on a sunny Florida morning in June. In about two hours the affected sprayed areas appeared dry, indicating lack of bacterial activity. A second application followed 24 hours later. After 30 days, no active bacterial sites appeared on the treated trees, and new growth seemed normally healthy. Even the smaller tree, though having seemed beyond salvaging, showed healthy new growth. Fruit dropping had ceased about a week after treatment. On untreated trees the noted symptoms worsened about as expected.

Zeolite dusts and sprays of this invention are simply formed and are similarly useful in abating or preventing the described plant infections and many others in the same or a similar manner.

A similar but separate test was conducted using phillipsite flooded with potassium cations ($K^+$) to displace its other cations then washed with distilled water until virtually all the potassium ions were displaced (deionization method). Particles (600–710 $\mu$m) of phillipsite so treated, including reduced in size, were then sprayed in the same manner upon trees similarly infected. The results were as before, no detectable differences.

The tolerance of citrus foliage to the concentration of the applied zeolite spray was tested up to 100 g/liter. No detectable difference was noted unless repeated spraying created a layer so thick as to restrict light enough to reduce assimilation. Minor, readily reversible damage in the form of chlorophyll-deficient spots may result if the spray contains particles larger than 300 um, as might occur regardless of composition from an inert spray containing any non-translucent particles so large as to bar normally incident light. No inhibition of gas exchange was noted.

Subsequent tests in the laboratory upon a related bacterium, *P. fluorescens,* did not exhibit any difference in bacterial inhibition whether dry-dusted, sprayed, or included in substrates, nor whether different types of agar were employed as the nutrient. Similarly successful results were obtained with clinoptilolite in place of the phillipsite, suggesting broad zeolitic effectiveness.

Similar laboratory experimentation was conducted upon several other types of microorganism. The results are depicted in FIGS. 1B (*Bacillus cereus*), 1C (*Escherichia coli*), and 1D (*Penicillium notatum*), the latter being a fungus. The plumes of growth in the untreated areas are especially well developed, whereas the treated areas are substantially devoid of such growth. Bacteria, having less organizational complexity than fungi, are more susceptible to disruption. Thus, the success against fungi indicated by FIG. 1D was obtained only with zeolitic material that had been deionized, as exemplified above in connection with the citrus tree treatment.

The more complex organization of animals, especially humans, suggests a relatively low probability of inhibition of human enzymes, by adsorption of ions essential to given enzyme activity. Hence, there is little likelihood of adverse systemic effects from administration of zeolites thereto, for whatever reason. Examples of specific localized successes in dentistry and medicine follow.

Dentistry. The patient's record showed an above average growth of plaque-building bacteria and mineral deposits on his teeth, also a history of chronic periodontal infection. For such reasons and because of several implants, the patient underwent an in-office treatment session every three months. Ten days before such a session the patient began brushing his teeth regularly with powdered phillipsite (≦150 um). At the check-up session, his teeth were found virtually free of plaque and mineral deposits, and his gums also were fine. Such startling improvement was credited to adsorption of the ions essential to enzymatic functioning of the various infections and also probable components in the formation of the mineral deposits.

According to this novel invention novel dentifrices or even temporary fillings may be formulated containing one or more finely divided zeolites, such as clinoptilolite or phillipsite, plus a filler, gel, or a paste or other ingredients as may be desired.

General Medicine. A living host may become infected with harmful bacteria, fungi, protozoa, and/or viruses by ingestion thereof in contaminated beverages or foodstuffs, the latter of which may have been recently alive and may serve as hosts for similar infections. Alternatively, a host may be infected by external contact with such harmful agents, especially at damage sites, such as cuts, bruises, or burns, where they can get established and proliferate, and from which they may migrate elsewhere within the host's body and even cause widespread systemic dysfunction.

The enzyme-inhibiting effect of zeolites or equivalent ion-exchangers or sorbants, such as clinoptilolite or phillipsite, for example, is evidenced as disinfection of the site with minimal or no scarring. Deionized zeolites are preferred over those in natural condition, because of greater efficacy against fungi and a broad range of bacterial and viral enzymes and/or their cofactors.

Veterinary Medicine. Infected animals sometimes exhibit loss of covering fur or hair, and often significant skin damage, as well, because of related scratching. As an example, substantial loss of hair accompanied by a wart-like growth on three quarters of the skin of an 80-pound cross-bred dog was diagnosed as of viral origin. Scratching also had damaged the skin significantly. A spray of phillipsite particles ($\leq 150$ $\mu$m, 100 g/liter) was applied to the body on alternate days.

Within the first twenty-four hours, the skin and lesions appeared dry in the treated regions, and the scratching abated significantly. Where treated, the disorder disappeared in ten days, and regrowth of hair was observed. After two weeks all lesions in the treated regions were healed and significant growth of hair had occurred. Extension to the rest of the body gave satisfactory results in a like time. Human skin infections can be expected to yield likewise without more specific identification.

Human Medicine. The sorbant effect of a zeolite upon the ions of enzymes essential to infection is not likely to result in acquisition of immunity by primitive microorganisms responsible for such infection. This is most important with viruses utilizing only a few enzymes activated by metal ions. A suitable example is the apoenzyme of HIV protease, which is activated by zinc cations. It seems virtually impossible that a fundamental mutation would occur so as to enable the apoenzyme to be activated by some other source. If the ion changed, the same or other zeolites would be likely to adsorb it also.

In contrast, HIV protease inhibitors, such as saquinavir or ABT387, are known to be deactivated rapidly in the host by cytochrome P450 enzymes, so only a small fraction of the inhibitor encounters the virus. The host system has to "metabolize" most of the inhibitor drug, incurring severe side effects. To counter them, the protease inhibitor may be administered in combination with another drug, such as ritonavir, which suppresses cytochrome P450 enzymes. It is highly desirable to identify inhibitors that operate directly upon viruses without likelihood of deactivation.

Notwithstanding that it is not known how the cytochrome enzymes identify the foreign chemicals, we can hypothesize with fair confidence that a zeolite, which does not react chemically and behaves—except for the adsorption—as an inert substance, will not be recognized by the cytochrome as xenobiotic and thus will not trigger any overload on the host's immune system. Too, the zeolite may be modified or synthesized in such a way that it cannot adsorb the specific metal cation of the cytochrome enzyme (iron cation in P450), so no interference would likely occur.

Manifestations of herpes, such as so-called cold sores and fever blisters (*H. febrilis*), also yield to topical treatment. Phillipsite in the form of wetted powder ($\leq 75$ $\mu$m) eliminated such skin infection in a day or less. Warts of viral origin were eliminated likewise in a longer time—about a week—of similar topical treatment. Such effective treatment was not known before.

This rationale has been implemented successfully in upper respiratory infection symptomatically diagnosed as "common cold" generally considered to be of viral origin. Simply breathing through a wet filter containing powdered phillipsite is moderately effective but also is relatively slow. Colloidal suspensions of phillipsite may be used as an inhalant to eliminate difficulty in breathing, and as a gargle to alleviate soreness of the throat. Concentrations of a few weight percent (e.g., 4%) are recommended for the aerosol, and somewhat higher (e.g., 10%) for the gargle.

No internal application of such a sorbant or ion-exchanger as a zeolite has been undertaken in connection with the present invention. However, as to ingestion, it should be noted that zeolite is a common additive in animal feed and has been found effective by Wells and Kilduff as reported in ZEOLITES (May 1985, 145–151) against gastro-intestinal infection of rats with the nematode *Nippostrongulus brasiliensis*.

Lung infections could be treated simply by perfusing the air from and to the lungs through an aqueous or like liquid suspension of powdered phillipsite, clinoptilolite, or other natural zeolite or equivalent natural or synthetic ion-exchanging composition, or through a wet granular bed thereof. If needed, a colloidal mist of zeolite could be provided, from time to time, for inhalation. If only air is to be perfused, it can be bubbled through a colloidal suspension of zeolite powder in a suitable liquid, or a wet bed, as is preferable for aggregations of people in confined spaces, such as in a conveyance or in a restaurant or theater.

Treatment of blood or other bodily fluids with zeolites so as to reach sites of viral infection, and the enzymes essential to such infection, could be accomplished by extracorporeal perfusion through a bed of natural or equivalent synthetic zeolite. This may be useful, whether alone or in conjunction with compatible pharmacological treatments of a more conventional nature, as a treatment for HIV or similar infections harming the immune system.

As noted, clinoptilolite and phillipsite are suitable natural zeolites for use in the practice of this invention. Some zeolites (such as erionite and mordenite, which are fibrous like asbestos) may not be so suitable. Although usually a suitable zeolite will be called upon to adsorb a cation, an anion may be targeted by a suitable ion-exchanger, whether a natural or synthetic zeolite or not. In specific, rather than generalized practice, a synthesized ion-exchanging or similar adsorbing composition may be selected. Special-purpose compositions may be designed for specific enzymes.

Natural zeolites may be used more or less directly from their mines, after reduction to suitable granular or particulate size plus screening out of contaminants by standard gravity methods, wet or dry (or both), as may be preferred. As already noted, dry heating, deionization, and re-ionization pretreatments may be employed to alter relative affinities for respective ion types.

Synthetic zeolites or equivalent (or better) ion-exchangers or sorbants may be prepared with enhanced affinity for classes of ions or for particular ions by methods analogous to those already used to prepare synthetic zeolites for other purposes.

Suitability for application to certain afflictions caused by rudimentary life forms or pre-life forms has been suggested above. Trypanosomal or other protozoan diseases of the blood may prove to be so treatable. Herpes zoster (shingles) and related viral diseases are candidates. A zeolite in liquid colloidal suspension may be injected into a blood stream to be transported to sites of remediable dysfunction, or into nearby tissue for a like purpose.

This invention also enables protection against interference with a host's functions that are dependent upon certain ions: for instance, in animals, deionization of a zeolite (or equivalent ion-exchanger) followed by re-ionization with a selected ion, such as iron cation, in order to block adsorption of iron cations from the host's hemoglobin; or, in plants, similar treatment of magnesium cations so as not to disturb the host's chlorophyllic functioning. Similar examples might be cited involving anions.

Preferred embodiments and variants have been suggested, and others may be made by adding, combining, deleting, or subdividing compositions, parts, or steps, while retaining some benefits of this invention, which itself is defined in the following claims.

The claimed invention:

1. A therapeutic composition substantially lacking metal ions, comprising a zeolite adapted to adsorb metal ions and, in finely divided form, effective upon topical application to the external surface of a living plant or animal host to remedy a dysfunctional condition visible as at least a surface irregularity thereon.

2. A plant canker remedy, comprising a therapeutic composition according to claim 1, in wet or dry sprayable form.

3. A skin disorder remedy, comprising a therapeutic composition according to claim 1, in wet or dry sprayable form.

4. A dental plaque remedy, comprising a therapeutic composition of claim 1, in gel or paste dentifrice form.

5. A zeolitic composition deionized of metal ions and thus useful to a living host at a site therein or thereon by adsorbing metal ions therefrom and thereby interfering with enzyme activity thereat that is at least potentially deleterious to the host and is dependent upon availability of such metal ions at such site.

6. A zeolitic composition according to claim 5, in finely divided therapeutically useful dry form.

7. A zeolitic composition according to claim 5, in finely divided therapeutically useful form dispersed in a liquid.

\* \* \* \* \*